US010424470B2

United States Patent
Tanner et al.

(10) Patent No.: US 10,424,470 B2
(45) Date of Patent: Sep. 24, 2019

(54) APPARATUS AND METHOD FOR MASS SPECTROMETRY

(71) Applicant: TOFWERK AG, Thun (CH)

(72) Inventors: Christian Tanner, Olten (CH); Martin Tanner, Bern (CH); Marc Gonin, Thun (CH)

(73) Assignee: TOFWERK AG, Thun (CH)

(*) Notice: Subject to any disclaimer, the term of this patent is extended or adjusted under 35 U.S.C. 154(b) by 0 days.

(21) Appl. No.: 15/560,692

(22) PCT Filed: Mar. 18, 2016

(86) PCT No.: PCT/EP2016/056030
§ 371 (c)(1),
(2) Date: Sep. 22, 2017

(87) PCT Pub. No.: WO2016/150875
PCT Pub. Date: Sep. 29, 2016

(65) Prior Publication Data
US 2018/0254176 A1 Sep. 6, 2018

(30) Foreign Application Priority Data

Mar. 25, 2015 (CH) .................................. 429/15

(51) Int. Cl.
H01J 49/00 (2006.01)
H01J 49/04 (2006.01)
(Continued)

(52) U.S. Cl.
CPC ........ H01J 49/0463 (2013.01); G01N 27/626 (2013.01); H01J 49/0404 (2013.01);
(Continued)

(58) Field of Classification Search
CPC ........ H01J 49/00; H01J 49/02; H01J 49/0027; H01J 49/0031; H01J 49/0036; H01J 49/105; H01J 49/10
(Continued)

(56) References Cited

U.S. PATENT DOCUMENTS 3,639,756 A * 2/1972 Schulz .................... H01J 9/022
250/281
4,833,322 A * 5/1989 Forster ................... G01N 21/73
250/288
(Continued)

FOREIGN PATENT DOCUMENTS

JP 61-195554 A 8/1986

OTHER PUBLICATIONS

"Digital delay line", Wikipedia, Feb. 26, 2014, retrieved from the Internet: URL: https://en.wikipedia.org/wiki/Digital_delay_line [retrieved on Jul. 22, 2015].
(Continued)

Primary Examiner — Jason L McCormack
(74) Attorney, Agent, or Firm — Birch, Stewart, Kolasch & Birch, LLP

(57) ABSTRACT

An apparatus for mass spectrometry comprises a portion generator (10) for creating localized analyte portions in synchronization with trigger pulses, a transfer system (20) coupled to the portion generator (10) for transporting the localized analyte portions, a plasma ionizer unit (30) coupled to the transfer system (20) for atomizing, vaporizing and ionizing received analyte portions with plasma, a mass analyzer (41) coupled to the plasma ionizer unit (30) for analyzing received analyte portions, the mass analyzer (41) comprising at least one detector, and a data acquisition electronics (50) connected to the at least one detector for acquiring signals (43) generated by the at least one detector.
(Continued)

The apparatus further includes a signal delay device (60) for receiving the trigger pulses (11) and delivering delayed signals (61) corresponding to the trigger pulses to account for a delay experienced by the particles to be analyzed between portion generation and detection.

24 Claims, 4 Drawing Sheets

(51) Int. Cl.
*H01J 49/10* (2006.01)
*G01N 27/62* (2006.01)
*H04L 1/16* (2006.01)
*H04L 1/18* (2006.01)

(52) U.S. Cl.
CPC ........ *H01J 49/0445* (2013.01); *H01J 49/105* (2013.01); *H04L 1/1664* (2013.01); *H04L 1/1678* (2013.01); *H04L 1/1841* (2013.01)

(58) Field of Classification Search
USPC ................................ 250/281, 282, 283, 288
See application file for complete search history.

(56) References Cited

U.S. PATENT DOCUMENTS

| | | | |
|---|---|---|---|
| 5,477,539 A | 12/1995 | Brown | |
| 6,933,497 B2* | 8/2005 | Vestal | H01J 9/025 |
| | | | 250/281 |
| 2005/0082471 A1* | 4/2005 | Kalinitchenko | H01J 49/105 |
| | | | 250/286 |
| 2010/0070817 A1 | 3/2010 | Heise | |
| 2013/0015345 A1 | 1/2013 | Vertes et al. | |
| 2013/0048852 A1* | 2/2013 | Verenchikov | H01J 49/0031 |
| | | | 250/282 |
| 2013/0181126 A1* | 7/2013 | Jong | G01N 35/10 |
| | | | 250/287 |
| 2014/0070085 A1* | 3/2014 | Molloy | H01J 49/105 |
| | | | 250/282 |
| 2014/0121117 A1 | 5/2014 | Tanner | |
| 2014/0353495 A1* | 12/2014 | Inagaki | G01N 21/714 |
| | | | 250/288 |
| 2015/0194296 A1* | 7/2015 | Verenchikov | H01J 49/0027 |
| | | | 250/282 |

OTHER PUBLICATIONS

"Mass cytometry", Wikipedia, Feb. 16, 2015, retrieved from the Internet: URL: https://en.wikipedia.org/wiki/Mass_cytometry [retrieved on Jul. 22, 2015].

Borovinskaya et al., "A prototype of a new inductively coupled plasma time-of-flight mass spectrometer providing temporally resolved, multi-element detection of short signals generated by single particles and droplets", J. Anal. At. Spectrom., 2013, vol. 28, pp. 226-233.

Borovinskaya et al., "Simultaneous Mass Quantification of Nanoparticles of Different Composition in a Mixture by Microdroplet Generator-ICPTOFMS", Anal. Chem., 2014, vol. 86, pp. 8142-8148.

Cui et al., "Depth profiling and imaging capabilities of an ultrashort pulse laser ablation time of flight mass spectrometer", Review of Scientific Instruments, 2012, vol. 83, pp. 093702-1 to 093702-7.

Gschwind et al., "Capabilities of inductively coupled plasma mass spectrometry for the detection of nanoparticles carried by monodisperse microdroplets", J. Anal. At. Spectrom., 2011, vol. 26, pp. 1166-1174.

Tanner et al., "A new ICP-TOFMS. Measurement and readout of mass spectra with 30 µs time resolution, applied to in-torch LA-ICP-MS", Anal Bioanal Chem, 2008, vol. 391, pp. 1211-1220.

Wang et al., "Fast Chemical Imaging at High Spatial Resolution by Laser Ablation Inductively Coupled Plasma Mass Spectrometry", Anal. Chem., 2013, vol. 85, pp. 10107-10116.

* cited by examiner

APPARATUS AND METHOD FOR MASS SPECTROMETRY

TECHNICAL FIELD

The invention relates to an apparatus for mass spectrometry comprising a portion generator for creating localized analyte portions in synchronization with trigger pulses, a transfer system coupled to the portion generator for transporting the localized analyte portions, a plasma ionizer unit coupled to the transfer system for vaporizing, atomizing and ionizing received analyte portions with plasma, a mass analyzer coupled to the plasma ionizer unit for analyzing received analyte portions, the mass analyzer comprising at least one detector and a data acquisition electronics connected to the at least one detector for acquiring signals generated by the at least one detector. The invention further relates to a method for mass spectrometry.

BACKGROUND ART

Inductively coupled plasma mass spectrometry (ICP-MS) is a type of mass spectrometry which is capable of detecting metals and several non-metals at concentrations as low as one part in $10^{15}$ (part per quadrillion, ppq) on non-interfered low-background isotopes. This is achieved by ionizing the sample with inductively coupled plasma and then using a mass analyzer to separate and quantify those ions. Compared to atomic absorption techniques, ICP-MS has greater speed, precision, and sensitivity.

The sample may be prepared by a number of methods. One preferred method is laser ablation, allowing for the elemental analysis of accurately defined spatial locations. In this method, a pulsed high power laser is focused on the solid sample and creates localized analyte portions, namely short pulses of ablated material which can be collected and entrained in a gas flow within a collection container and then be swept into the plasma.

Another method of preparation of the sample is the generation of single droplets (or micro-droplets). This may be achieved by piezo-electrically driven dispenser heads, such as described in O. Borovinskaya, B. Hattendorf, M. Tanner, S. Gschwind, D. Günther, "A prototype of a new inductively coupled plasma time-of-flight mass spectrometer providing temporally resolved, multi-element detection of short signals generated by single particles and droplets", J. Anal. At. Spectrom., 2013, 28, 226-233.

A transfer system is arranged between the laser ablation device or the droplet generator (DG), respectively and the ICP unit. It allows for transferring the pulses of ablated material to the ICP unit. It may comprise a transfer tube and/or a device embedding the particles in a gas jet for the transfer. Further, it comprises a connection to the ICP gas input.

In the ICP unit, the aerosol or droplet is vaporized, atomized and ionized and then transferred to the mass analyzer.

There is a substantial time delay, the Signal Delay, between the trigger pulse triggering the laser ablation or the droplet generation and the appearance of the corresponding ions at the entrance of the mass analyzer. In a conventional LA-ICP-MS or DG-ICP-MS this delay is not compensated or accounted for. The measurement is started and the signal is continuously acquired for some time. This method is not optimal, because the assignment of each signal peak to the corresponding laser pulse or droplet generation has to be made in a post processing step. Integration of each peak signal is also best done in post processing, since real time integration would rely on the laser or trigger clock and the acquisition clock being perfectly synchronized. In practice the two clocks will slightly diverge which will cause Moiré patterns to appear in the data.

Further, in the case of laser ablation, if the sample is moved under the laser during measurement (a so-called "line scan"), the positional information corresponding to each laser shot is only approximate, as calculated from the time after the start of measurement.

The Signal Delay and the post-processing thus introduces further computational burden, makes the processing slower and may affect the precision of the results.

SUMMARY OF THE INVENTION

It is the object of the invention to create an apparatus and a method pertaining to the technical field initially mentioned, that provide a reduction of computational load, allow faster processing and provide reliable results.

The solution of the invention is specified by the features of claims 1 and 18. According to the invention, the apparatus comprises a signal delay device for receiving the trigger pulses and delivering delayed signals corresponding to the trigger pulses to account for a delay experienced by the analyte portions to be analyzed between portion generation and detection.

Similarly, in the context of an inventive method, trigger pulses are received by a delay device, delayed signals corresponding to the trigger pulses are generated and included in the analysis of the acquired signals to account for a delay experienced by the analyte portions to be analyzed between portion generation and detection.

In general, the delay designates the length of a time period between the trigger pulse and the start of the data acquisition. It may be caused by effects arising in the portion generator, the transfer system, the ICP unit and/or the ion transfer optics to the mass analyzer.

The method and apparatus allow for synchronising the data acquisition with each generation of a portion. In this manner, the exact time and position of each portion is known, as is the data which corresponds to each portion. Correct data maps can be presented in real time, since the time consuming post processing steps for assigning data peaks to portion generation events and integrating data are no longer required. Also, every portion generation event will be covered by the same number of TOFMS extractions and therefore the data of every portion looks identical. This facilitates subsequent data analysis tremendously.

This superior timing is accomplished by synchronizing every portion generation event with an acquisition sequence of the TOFMS, wherein the signal delay device accounts for the Signal Delay. After the Signal Delay, data is acquired for a limited time, corresponding to the duration of useful signal.

Preferably, the plasma ionizer unit is an inductively coupled plasma (ICP) unit for vaporizing, atomizing and ionizing received analyte portions with inductively coupled plasma.

However, the invention is not restricted to ICP units, microwave plasma ion sources or laser plasma ion sources may be employed as well.

Preferably, the signal delay device is an overlapping signal delay device capable of simultaneously processing a plurality of trigger pulses. This allows for handling situations where the signal delay is more than a time between portion generation events. Accordingly, high frequencies in the generation of analyte portions may be handled, which allows for much faster measurements.

In a first variant of the invention, the creation of the localized analyte portions is controlled by the trigger pulses. Thus, the trigger pulses are used to control the creation of the localized analyte portions by controlling the corresponding device, such as the laser of the laser ablation device or the droplet generator. In this variant, the trigger pulses will be usually generated by a component of the laser ablation device or the droplet generator, respectively. Accordingly, the portion generator is the master device.

In a second variant of the invention, the trigger pulses are generated by a timing generator controlling the mass analyzer and delivered to the portion generator as well as to the signal delay device. Accordingly, the mass analyzer is the master device.

Whether the first or the second variant is the better choice, depends on the portion generator as well as the mass analyzer used, as certain types of portion generators and mass analyzers are more easily triggered than others.

In a preferred embodiment, the signal delay device is connected to the data acquisition electronics of the mass analyzer for delivering the delayed signals corresponding to the trigger pulses to the data acquisition electronics.

Preferably, the delayed signals received at the data acquisition electronics enable the data acquisition. This means that data acquisition cycles are started depending on the received delayed signals. In this case, the mass analyzer operates continuously, but a data acquisition sequence is started depending on the delayed signals.

In a further preferred embodiment, the delayed signals received at the data acquisition electronics are used as a tag in a data stream generated by the data acquisition electronics to tag data corresponding to a certain analyte portion. In this case, data acquisition runs continuously.

In a further preferred embodiment, the delayed signals are delivered to the mass analyzer and are used for enabling the mass analyzer. This has the advantage that the measurement of the mass analyzer (e. g. a time-of-flight extraction period) is synchronized with the arrival of the analyte portion, whereas in the case of a continuously running mass analyzer, jitter in the order of the length of a single measurement cycle (e. g. extraction period) will occur. However, continuous operation may be preferable with many mass analyzers.

In a preferred embodiment of the inventive apparatus, the portion generator is a laser ablation device, the trigger pulses are laser trigger pulses and the localized analyte portions are pulses of aerosol.

In another preferred embodiment of the inventive apparatus, the portion generator is a droplet generator, the localized analyte portions are single droplets generated on demand by the droplet generator, triggered by the trigger pulses. The droplet generator receives liquid substances to be analyzed and generates droplets having a predetermined size from the liquid. The liquid substances may contain solid particles such as nano particles dispersed in a carrier liquid, and the carrier liquid may be used for calibration purposes. Most preferably, the droplet generator generates micro droplets. Commercial micro-droplet dispenser heads are available such as the type MD-K-150 with control unit MD-E-201-H of Microdrop Technologies GmbH, Norderstedt, Germany, as described in O. Borovinskaya et al. cited above.

The localized analyte portion may contain several constituents, namely the actual analyte as well as further substances such as solvents, carrying fluids or substances for calibration.

In a preferred embodiment, the mass analyzer is a mass spectrometer, in particular a time-of-flight mass spectrometer. This allows for very fast measurements, high mass accuracy and mass resolution.

Other mass analyzers may be employed such as e. g. quadrupole mass filters.

In particular, the transfer system is a pneumatic system comprising a directed gas stream which may be in a transfer tube, an output of the transfer tube being connected to a gas input of the ICP unit.

The Signal Delay may be more than the time between portion generation events, the trigger period. In one implementation, the Signal Delay is typically in the range of several 100 ms whereas the laser period is typically in the range of 10 ms. This means up to 10 sample events will be under way to the acquisition system at any time. Other implementations may have more or less events in flight at one time.

To cope with this fact, in order to account for delays that exceed a period of the trigger pulses, in a preferred embodiment of the invention in order to reproduce the trigger sequence entirely and completely, but at a later time, a delay line (DL) is employed. In general, delay lines can be used to reproduce digital or analog signals. Suitable analog and digital delay lines are commercially available.

A simple 1-bit digital DL can be constructed from a shift register. Setting the input bit starts the delay. This bit is shifted through the register until it appears at the last position of the register. By reading the state at each register position, the delay can be set to any multiple of the clock cycle up to (N−1) times the clock period, where N is the register size. Since shift registers can be constructed from computer memory chips, the possible size is extremely large. This allows for very long delays and/or very fast clock rates (high timing resolution).

Digital delay lines can reproduce more complicated signals than a 1-bit 0/1. Furthermore, digital delay line units with the desired millisecond resolution are also widely available for various applications.

Another form of digital DL can be realized in software. Either a general purpose microprocessor or a dedicated unit such as a FPGA can equivalently be used.

Software DL are widely used in many fields and are a part of many digital signal processing packages. For example, many audio effects (reverberation, chorus, etc) are based on delayed signals.

In a preferred embodiment, a processor is programmed to generate time stamps based on trigger pulses, to deliver the time stamps to a FIFO buffer, to read out the time stamps from the FIFO buffer and to generate an output signal if a read out time stamp plus a user definable delay corresponds to a present time.

This is functionally equivalent to the 1-bit shift register DL mentioned above. It takes a pulse as input and gives a pulse as output. It is asynchronous since the FIFO is not incremented at each clock, but depends on a comparison.

The comparison of the time stamp with the present time and the delay may be effected in different ways. As an example, the delay may be subtracted from the clock or added to the timestamp in the FIFO buffer.

In another preferred embodiment, a processor is programmed to deliver a signal for each received trigger pulse to a FIFO buffer, wherein a length of the FIFO buffer is chosen to correspond to a user definable delay in clock cycles, wherein the processor is programmed to propagate entries of the FIFO buffer by one position for every clock cycle and wherein an output signal is generated each time a signal reaches an output of the FIFO buffer. This method is synchronous. The FIFO is made as long as the desired delay in clock cycles, and triggers are propagated through it at every clock cycle. This is equivalent to the shift register DL both in function and in internal principle of operation.

The clock may also be software defined rather than a hardware clock, to vary the delay range and resolution.

In principle, instead of a delay line as described before, the signal delay device comprises at least one delay generator. This component receives an input signal (i. e. one of the trigger pulses) and transmits an output signal after a predetermined (user definable) delay after reception of the input signal. In general, a delay generator may not be triggered again during the delay period, i. e. only input signals are processed that arrive after expiry of the delay period of the preceding input signal.

In order to account for delays that exceed a period of the trigger pulses, two or more delay generators may be employed. The first delay generator provides a delay up to the trigger period minus a small increment. It triggers a second delay generator which provides the remaining delay. This concept can be extended to an arbitrary number of delay generators.

The arrangement of a number of delay generators may be based on an array of programmable delay generators. Programmable delay generators (PDG) are available as complete, inexpensive integrated circuit packages. An array of PDG with a simple interface may be easily constructed on a small printed circuit board.

Other advantageous embodiments and combinations of features come out from the detailed description below and the totality of the claims.

BRIEF DESCRIPTION OF THE DRAWINGS

The drawings used to explain the embodiments show.

Figure 1:
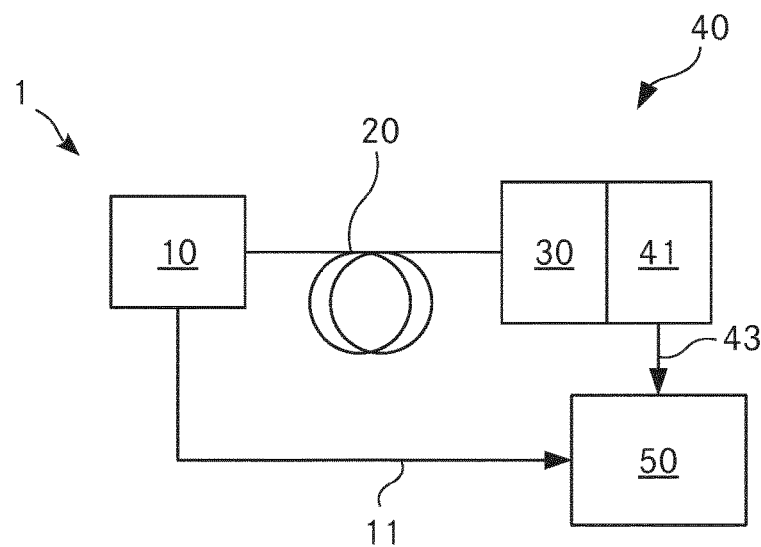
FIG. 1 A functional diagram of a conventional LA-ICP-MS.

In the figures, the same components are given the same reference symbols.
Preferred Embodiments The FIG. 1 shows a functional diagram of a conventional apparatus for laser ablation inductively coupled plasma mass spectrometry (LA-ICP-MS). The apparatus 1 comprises a laser ablation unit 10, a pneumatic transfer system 20 comprising a collection container above the sample, a transfer tube and a connection to a gas input of an ICP (inductively coupled plasma) unit 30 of a mass spectrometer 40. In the ICP unit 30, the particles are vaporized, atomized and ionized. The output of the ICP unit 30 is connected to a mass analyzer 41, in particular a time-of-flight mass spectrometer, for analyzing the (laser generated) aerosol using a method known as such. The signal 43 obtained from a detector of the mass spectrometer 40 is forwarded to data acquisition (DAQ) electronics 50. The same applies to the laser trigger signal 11, which is forwarded to the DAQ electronics 50 from the laser ablation unit 10.

Figure 2:
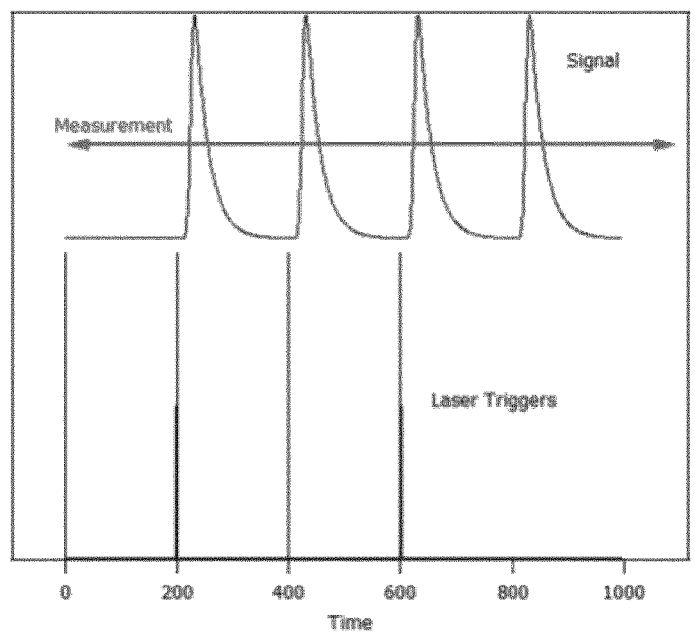
FIG. 2 the measurement sequence of conventional LA-ICP-MS acquisition.

The FIG. 2 shows the measurement sequence of conventional LA-ICP-MS acquisition, i. e. an acquisition process that does not account for the time-varying nature of the signal. The measurement may be synchronized at some time point before or at the first trigger, but not with subsequent triggers.

Figure 3:
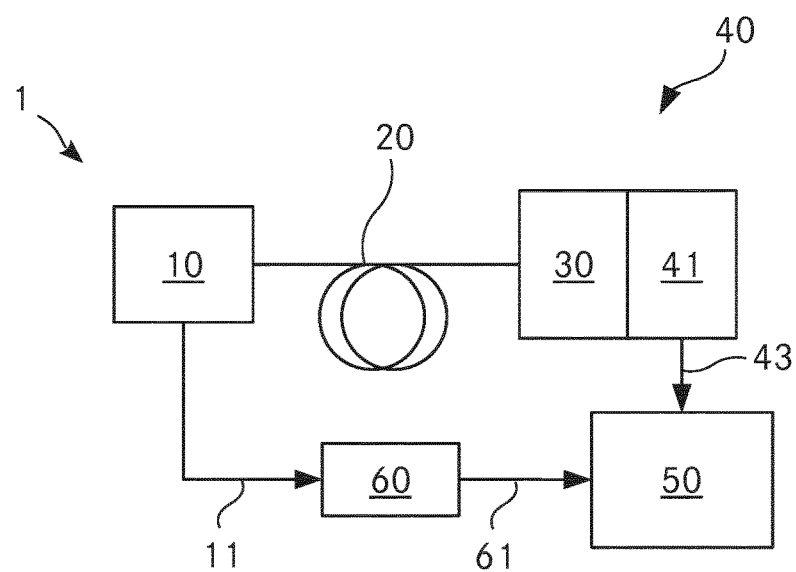
FIG. 3 a functional diagram of a first embodiment of the invention.

The FIG. 3 shows a functional diagram of a first embodiment of the invention that allows for synchronisation with every laser shot. In many aspects, the apparatus corresponds to the apparatus shown in FIG. 1. However, the laser trigger signal 11 is not directly forwarded to the DAQ electronics 50 from the laser ablation unit 10, but a signal delay device 60 is arranged in between the laser ablation unit 10 and the DAQ electronics 50. The signal delay device 60 receives the laser trigger signal 11 and forwards a delayed signal 61 that essentially corresponds to the laser trigger signal 11 but is delayed by a user definable amount in order to account for the delay experienced by the particles to be analyzed between laser ablation in the laser ablation unit 10 and detection by the detector of the mass spectrometer 40.

In an alternative embodiment, the apparatus comprises a droplet generator instead of the laser ablation unit, a pneumatic transfer system connected to a collection container above the sample, a transfer tube and a connection to a gas input of an ICP (inductively coupled plasma) unit. In the ICP unit, the particles are vaporized, atomized and ionized. The output of the ICP unit is connected to a mass analyzer, in particular a time-of-flight mass spectrometer, for analyzing the vaporized, atomized and ionized droplets using a method known as such. The signal obtained from a detector of the mass analyzer is forwarded to data acquisition (DAQ) electronics. Accordingly, a basic system similar to that described in O. Borovinskaya et al. cited above is used. In addition, the trigger signal of the droplet generator is forwarded to a signal delay device arranged in between the droplet generator and the DAQ electronics. The signal delay device receives the trigger signal and forwards a delayed signal that essentially corresponds to the trigger signal but is delayed by a user definable amount in order to account for the delay experienced by the particles to be analyzed between droplet generation in the droplet generator and detection by the detector of the mass analyzer.

Figure 4:
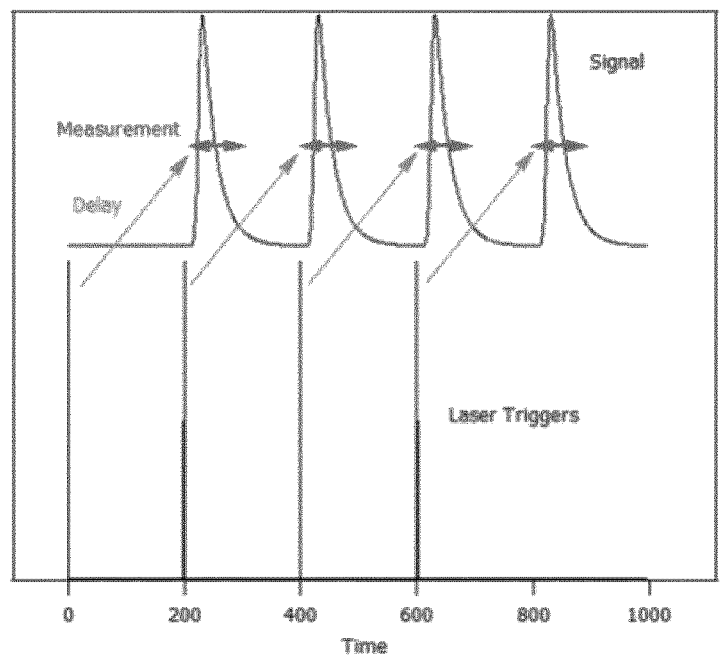
FIG. 4 the measurement sequence according to the invention.

The FIG. 4 shows the corresponding improved measurement sequence according to the invention. It is to be noted that the intervals between triggers are not necessarily constant. The delay from a trigger to the signal depends on the instrument settings, but is constant for one set of operating conditions (gas flows, tube length, etc.).

Figure 5:
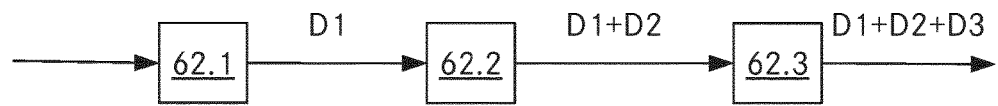
FIG. 5 a functional diagram relating to an embodiment of an inventive apparatus using cascaded programmable delay generators.

The FIG. 5 is a functional diagram relating to an embodiment of an inventive apparatus using cascaded programmable delay generators. The diagram shows three programmable delay generators (PDG) 62.1, 62.2, 62.3 imparting a delay of D1, D2 and D3, respectively. Each PDG 62.1 . . . 3 is used to generate a delay from 0 to the minimum trigger period minus a small increment and to trigger the next PDG 62.2, 62.3. The total delay as shown is up to 3 trigger periods, and the system can accept up to three triggers until the signal relating to the first trigger is forwarded to the DAQ electronics. A higher number of triggers may be accepted if the number of PDG 62.1 . . . 3 is increased.

Figure 6:
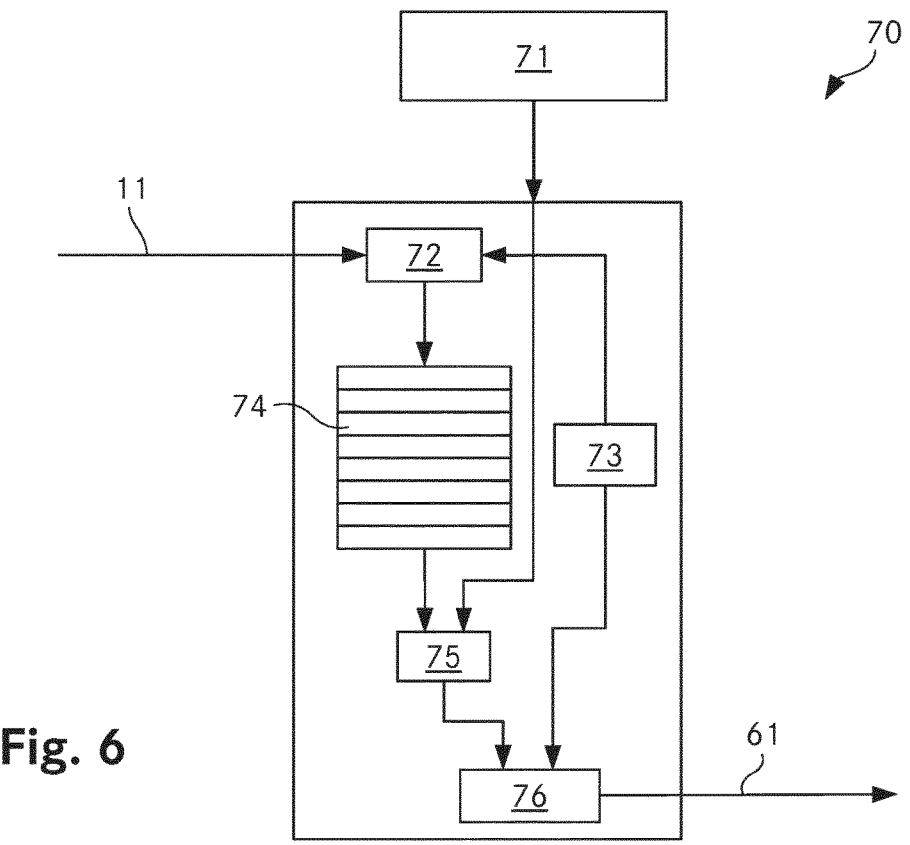
FIG. 6 a functional diagram of a digital delay line according to the invention, realized in software.

The FIG. 6 is a functional diagram of a digital delay line according to the invention, realized in software. The digital delay line 70 receives the trigger signal 11 from the laser ablation unit or droplet generator, respectively. It further receives a user programmable delay 71 (for example, in one implementation the range is typically 1 ms to 1'000 ms) through a suitable interface (RS 232, TCP/IP LAN, CAN bus etc.).

For each received trigger in the trigger signal 11 a time stamp is generated (step 72) based on an internal clock 73. The time stamps are filled into a timestamp FIFO buffer 74. The delay 71 is added to the time stamp which is the first in the queue of the FIFO buffer 74 (step 75). If the added time matches the current time of the clock 73 (step 76), a signal 61 is generated and forwarded to the DAQ electronics.

This is functionally equivalent to a 1-bit shift register delay line. It takes a pulse as input and gives a pulse as output. It is asynchronous since the FIFO is not incremented at each clock, but depends on a comparison.

The invention is not restricted to this particular embodiment. For example the delay could be subtracted from the clock instead of added to the FIFO output. The method could also be made synchronous instead of asynchronous, in that the FIFO is made as long as the desired delay in clock cycles, and triggers are propagated through it at every clock cycle. This is again equivalent to the shift register delay line both in function and in internal principle of operation.

The clock may also be software defined rather than a hardware clock, to vary the delay range and resolution.

Figure 7:
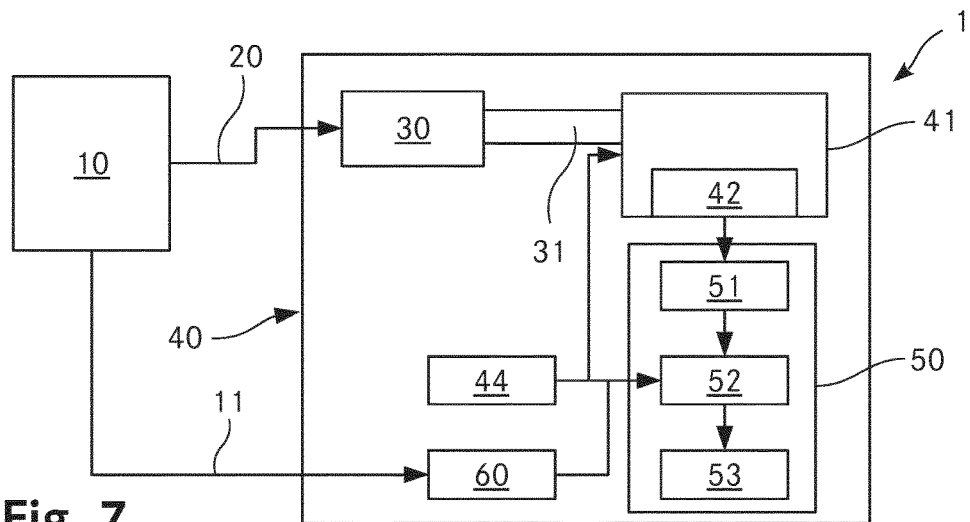
FIG. 7 a block diagram of the first embodiment.

The FIG. 7 is a block diagram of the first embodiment. It shows the apparatus 1 with the laser ablation unit 10, a pneumatic transfer system 20 connected to the gas input of the ICP (inductively coupled plasma) unit 30. The latter is part of the mass spectrometer 40 and coupled to a time-of-flight mass analyzer 41 by means of an interface 31. The mass analyzer 41 features a detector 42 coupled to the data acquisition (DAQ) electronics 50. The latter comprises a pre-amplifier 51 for amplification of the signal 43 generated by the detector 42, a data acquisition module 52 and a computer 53 for processing the data received from the data acquisition module 52.

The mass spectrometer 40 further comprises a timing generator 44 for controlling the mass analyzer 41 and the data acquisition module 52.

In the first embodiment, the delay generator 60 receives the laser trigger signals 11 from the laser ablation unit 10 and generates delayed signals 61 as described above. The delayed signals 61 are fed to the data acquisition module 52. This allows for activation of the data acquisition in synchronization with the arrival of the analyte portions or for setting a tag in a data stream generated by the data acquisition module 52 to indicate the correspondence with a certain analyte portion.

Figure 8:
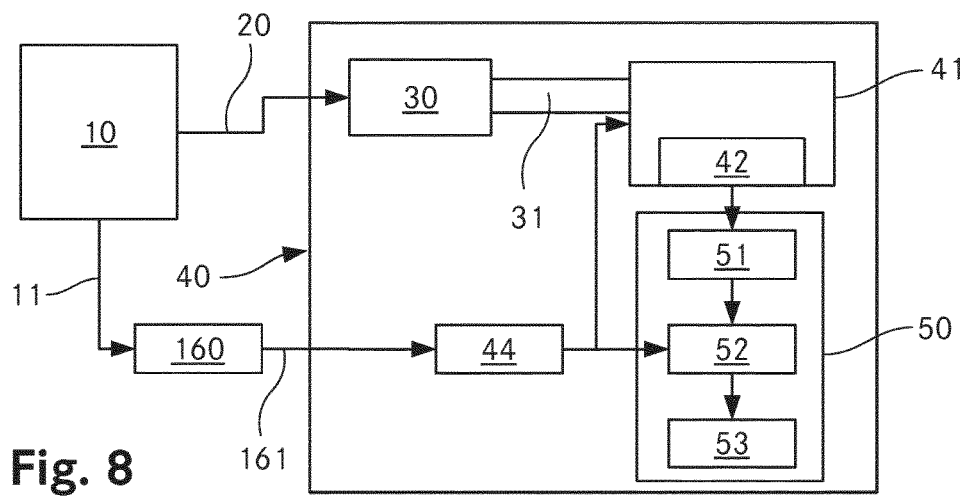
FIG. 8 a block diagram of a second embodiment of the invention.

The FIG. 8 is a block diagram of a second embodiment of the invention. Many elements correspond to those of the first embodiment. It is thus not required to describe them once more. In contrast to the first embodiment, the delay generator 160 receiving the laser trigger signals 11 from the laser ablation unit 10 is connected to an input of the timing generator 44 of the mass spectrometer 40. The latter controls the mass analyzer 41 as well as the data acquisition module 52 depending on the received delayed signals 161 from the delay generator 160. Accordingly, not only acquisition but the mass analysis is performed in synchronization with the arrival of the analyte portions.

Figure 9:
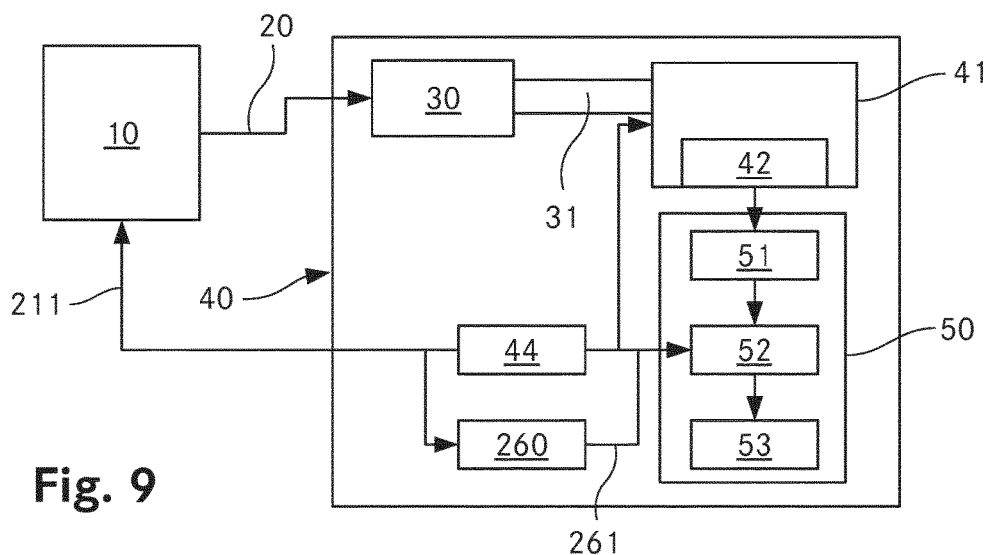
FIG. 9 a block diagram of a third embodiment of the invention.

The FIG. 9 is a block diagram of a third embodiment of the invention. Again, many elements correspond to those of the first and second embodiment. It is thus not required to describe them once more. In contrast to the first and second embodiment, the delay generator 260 receives an input signal from the timing generator 44 of the mass spectrometer 40. Furthermore, the laser ablation unit 10 is as well controlled by the timing generator 44. Similar to the first embodiment, the delayed signals 261 generated by the delay generator 260 are fed to the data acquisition module 52. Again, this allows for activation of the data acquisition in synchronization with the arrival of the analyte portions or for setting a tag in a data stream generated by the data acquisition module 52 to indicate the correspondence with a certain analyte portion.

In summary, it is to be noted that the invention creates an apparatus and a method for mass spectrometry that provide a reduction of computational load, allow faster processing and provide reliable results.

The invention claimed is:

1. Apparatus for mass spectrometry, comprising
a portion generator for creating localized analyte portions in synchronization with trigger pulses;
a transfer system coupled to the portion generator for transporting the localized analyte portions;
a plasma ionizer unit coupled to the transfer system for vaporizing, atomizing and ionizing received analyte portions with plasma;
a mass analyzer coupled to the plasma ionizer unit for analyzing elemental content of received analyte portions, the mass analyzer comprising at least one detector;
a data acquisition electronics connected to the at least one detector for acquiring signals generated by the at least one detector;
a signal delay device for receiving the trigger pulses and delivering delayed signals corresponding to the trigger pulses to account for a delay experienced by the analyte portions to be analyzed between portion generation and detection, thereby allowing for synchronising the data acquisition with each generation of an analyte portion in that the exact time and position of each analyte portion is known, as is the data which corresponds to each analyte portion,
wherein the signal delay device is connected to the data acquisition electronics of the mass analyzer for delivering, the delayed signals corresponding to the trigger pulses to the data acquisition electronics
wherein the signal delay device is an overlapping signal delay device capable of simultaneously processing a plurality of trigger pulses.

2. Apparatus as recited in claim 1, wherein the plasma ionizer unit is an inductively coupled plasma unit for vaporizing, atomizing and ionizing received analyte portions with inductively coupled plasma.

3. Apparatus as recited in claim 1, wherein the plasma ionizer unit is a microwave plasma ion source.

4. Apparatus as recited in claim 1, wherein the plasma ionizer unit is a laser plasma ion source.

5. Apparatus as recited in claim 1, wherein the creation of the localized analyte portions is controlled by the trigger pulses.

6. Apparatus as recited in claim 1, wherein the trigger pulses are generated by a timing generator controlling the mass analyzer and delivered to the portion generator and to the signal delay device.

7. Apparatus as recited in claim 1, wherein the delayed signals received at the data acquisition electronics enable the data acquisition.

8. Apparatus as recited in claim 1, wherein the delayed signals received at the data acquisition electronics are used as a tag in a data stream generated by the data acquisition electronics to tag data corresponding to a certain analyte portion.

9. Apparatus as recited in claim 1, wherein the delayed signals are delivered to the mass analyzer and used for enabling the mass analyzer.

10. Apparatus as recited in claim 1, wherein the portion generator is a laser ablation device, that the trigger pulses are laser trigger pulses and that the localized analyte portions are pulses of aerosol.

11. Apparatus as recited in claim 1, wherein the portion generator is a droplet generator, the localized analyte portions are single droplets generated on demand by the droplet generator, triggered by the trigger pulses.

12. Apparatus as recited in claim 1, wherein the mass analyzer is a mass spectrometer.

13. Apparatus as recited in claim 1, wherein the transfer system is a pneumatic system comprising a collection container and a transfer tube, an output of the transfer tube being connected to a gas input of the plasma ionizer unit.

14. Apparatus as recited in claim 1, wherein the signal delay device comprises a delay line.

15. Apparatus as recited in claim 14, wherein the delay line is a digital delay line.

16. Apparatus as recited in claim 15, wherein the digital delay line is realized in software.

17. Apparatus as recited in claim 16, wherein a processor is programmed to generate time stamps based on trigger pulses, to deliver the time stamps to a FIFO buffer, to read out the time stamps from the FIFO buffer and to generate an output signal if a read out time stamp plus a user definable delay corresponds to a present time.

18. Apparatus as recited in claim 16, wherein a processor is programmed to deliver a signal for each received trigger pulse to a FIFO buffer, wherein a length of the FIFO buffer is chosen to correspond to a user definable delay in clock cycles, wherein the processor is programmed to propagate entries of the FIFO buffer by one position for every clock cycle and wherein an output signal is generated each time a signal reaches an output of the FIFO buffer.

19. Method for mass spectrometry, comprising the steps of:
creating localized analyte portions, controlled by trigger pulses,
transferring the localized analyte portions to a plasma ionizer unit,
vaporizing, atomizing and ionizing received analyte portions by the plasma ionizer unit,
processing received ionized elemental content of the analyte portions by a mass analyzer, including the step of detecting the processed analyte at a detector;
acquire signals received from the detector and analyzing the acquired signals;
characterized by receiving the trigger pulses by a delay device, generating delayed signals corresponding to the trigger pulses and including the delayed signals in the analysis of the acquired signals to account for a delay experienced by the analyte portions to be analyzed between creation and detection, thereby allowing for synchronising the data acquisition with each generation of an analyte portion in that the exact time and position of each analyte portion is known, as is the data which corresponds to each analyte portion,
wherein a signal delay is more than a time between portion generation events and in that the delay device simultaneously processes a plurality of trigger pulses.

20. Method as recited in claim 19, wherein the localized analyte portions are pulses of aerosol created by laser ablation and that the trigger pulses are laser trigger pulses.

21. Method as recited in claim 19, wherein the localized analyte portions are single droplets created on demand by a droplet generator, triggered by the trigger pulses.

22. Apparatus as recited in claim 12, wherein the mass analyzer is a time-of flight mass spectrometer.

23. Apparatus as recited in claim 1, wherein the signal delay device accounts for a signal delay between the trigger pulses and appearance of the corresponding ions at an entrance of the mass analyzer, wherein the signal delay device being an overlapping signal delay device capable of simultaneously processing a plurality of trigger pulses allows for handling situations where the signal delay is more than a time between portion generation events.

24. Apparatus as recited in claim 1, wherein the delayed signals are feedable to the data acquisition electronics, allowing for activation of the data acquisition in synchronisation with the arrival of the analyte portions or for setting, a tag, in a data stream generated by the data acquisition electronics to indicate the correspondence with a certain analyte portion.

* * * * *